United States Patent [19]

Denis et al.

[11] Patent Number: 4,560,490

[45] Date of Patent: Dec. 24, 1985

[54] DISPERSING ADDITIVE COMPOSITIONS FOR LUBRICATING OILS AND THEIR MANUFACTURE

[75] Inventors: Jacques Denis, Charbonniere Les Bains; Michel Senneron, Meylan; Bernard Sillion, Rocquencourt, all of France

[73] Assignee: Institut Francais du Petrole, Rueil-Malmaison, France

[21] Appl. No.: 576,651

[22] Filed: Feb. 3, 1984

[30] Foreign Application Priority Data

Feb. 4, 1983 [FR] France ............................... 83 01918

[51] Int. Cl.$^4$ .......................... C10M 1/32; C10M 1/20
[52] U.S. Cl. ............................. 252/51.5 A; 260/501.2
[58] Field of Search ................ 252/51.5 A; 260/501.2

[56] References Cited

U.S. PATENT DOCUMENTS 3,219,666  11/1965  Norman et al. ...................... 260/268
3,272,746   9/1966  Le Suer et al. ...................... 252/47.5

FOREIGN PATENT DOCUMENTS 2264084  3/1975  France .

*Primary Examiner*—Jacqueline V. Howard
*Attorney, Agent, or Firm*—Millen & White

[57] ABSTRACT

An additive composition having a dispersing effect in lubricating oils is obtained by reacting at least one substituted succinic anhydride with at least one alkylphenol and with hexamethylene tetramine, preferably in respective proportions of from 1 to 2 moles of substituted succinic anhydride per mole of the alkylphenol and from 1.2 to 2 amino equivalents of hexamethylene tetramine per mole of the substituted succinic anhydride.

18 Claims, No Drawings

4,560,490

DISPERSING ADDITIVE COMPOSITIONS FOR LUBRICATING OILS AND THEIR MANUFACTURE

BACKGROUND OF THE INVENTION

This invention has as objects to provide new oil-soluble dispersing compositions, a process for the manufacture thereof, and lubricants containing said compositions. More particularly, this invention relates to new oil soluble dispersing compositions produced by reacting a substituted succinic anhydride with hexamethylene tetramine and an alkyl phenol.

One of the main problems now encountered in engine lubricants is due to the unavoidable presence in the lubricant of extraneous particles in suspension, such as carbonaceous substances and sludges emanating from soots, from products of fuel and lubricant deterioration, and from water.

The accumulation of these suspended substances seriously affects the lubricant efficiency in the engine and it is thus important to prevent the agglomeration and the deposition of these undesirable substances, as varnishes, hard carbonaceous materials and sludges, in the different parts of the engine. For several years, attempts have been made to cope with these difficulties by using organo-metallic additives, such as, for example, sulfonates, phenates or salicylates of alkaline-earth metals, or organic additives such as, for example, polymethacrylates, either grafted or copolymerized with nitrogenous unsaturated reactants, or succinimides of polyethylenepolyamines.

However, the use of organo-metallic additives is limited by the likelihood of deposition of various metal oxides onto the electrodes of the sparkplugs in spark-ignition engines; the resultant deposits may cause pre-ignition which is detrimental to the engine. The known ashless organic additives suffer from the disadvantage of a limited efficiency at high temperature.

Thus, the French patent application FR No. 2 264 084 discloses detergent additives for lubricating oils which may be obtained by reacting hexamethylene tetramine with an alkylphenol having at least one of the positions 2, 4 and 6 of the aromatic ring unsubstituted.

The U.S. Pat. No. 3,962,104 discloses ashless detergent additives for lubricants consisting of quaternary ammonium salts, formed by the reaction of a tertiary amine (e.g. hexamethylene tetramine) with an olefin oxide in the presence of an excess of water, followed by the reaction with an organic acid compound which may be, for example, a substituted succinic anhydrice (dodecenyl-succinic anhydride or polyisobutenylsuccinic anhydride) or an alkylphenol.

SUMMARY OF THE INVENTION

The object of the invention is to provide new compositions of dispersing additives efficient in lubricants and which do not suffer from the abovementioned disadvantages.

As a general rule, the additive compositions of the invention may be defined as the products obtained by the simultaneous reaction of a substituted succinic anhydride with hexamethylene tetramine and an alkyl phenol.

DETAILED DISCUSSION

More particularly, the substituted succinic anhydrides used for preparing the additives of the invention are those which are obtained:

- by condensation of a maleic anhydride with an unsaturated, linear or branched, olefinic or polyolefinic, hydrocarbon having at least one unsaturation per molecule, and comprising from 5 to 250 carbon atoms (preferably from 60 to 120);
- by condensation of a maleic anhydride with a halogenated olefin or polyolefin, the olefin or polyolefin being defined as above; or
- by any other process known to produce the products usually defined as: alkenylsuccinic anhydrides or polyalkenylsuccinic anhydrides.

The substituted succinic anhydride is advantageously obtained by reacting a polymer of monoolefin having 2 to 5 carbon atoms with maleic anhydride, said polymer having generally a molecular weight of about 500 to 1600, more particularly about 700 to 1300. Such polymers have the advantage of being easily available at low cost. Preferred examples are polyisobutenes.

Alkylphenols used to prepare the additives compositions according to the invention consist more particularly of substituted phenols having one or more linear or branched alkyl groups with 4 to 12 carbon atoms, these alkyl groups being either in ortho and/or in para position with respect to the phenol group. Preferred examples of alkylphenols are: p.nonylphenol, o.nonylphenol, p.dodecylphenol, o.dodecylphenol, 2,4-di tert-butyl and 2,6 di tert-butylphenols, p.hexylphenol, p.heptylphenol and p.octylphenol.

The additives according to the invention are produced by admixing the above-defined reactants in proportions generally corresponding to a molar ratio of the succinic anhydride to the substituted alkylphenol from about 1/1 to 2/1, and to an excess of hexamethylenetetramine with respect to the substituted succinic anhydride. The amount of hexamethylenetetramine generally corresponds to 1.2 to 2 amine groups per mole of substituted succinic anhydride, i.e. from 0.3 to 0.5 mole of hexamethylenetetramine per mole of substituted succinic anhydride.

The reaction is generally conducted at a temperature from 120° to 250° C., preferably from 180° to 210° C., for 1 to 3 hours and, preferably, for 1 h 30 to 2 h 30 minutes. It is performed either in the absence of solvent or in oil in such an amount that the final product contains about 50% by weight of active substance.

When the operation is conducted in the absence of solvent, the reaction product may be subsequently dissolved in oil, so as to obtain a solution of suitable viscosity; a filtration or a washing with water or a degasing by bubbling with inert gas may also be performed in order to remove the unreacted hexamethylene tetramine and its decomposition products.

The additive compositions of the invention are generally used in lubricants either alone or in combination with other conventional additives. When used as dispersing additives in oil, their proportions may range from 0.1 to 20% by weight of the lubricant, depending on the type of use of this lubricant and on the optional presence of other specific dispersant and/or detergent additives. Usually, their proportions will range from 1 to 10% by weight of the lubricant.

The compositions of the invention may be incorporated to various oil bases, either natural, synthetic or mixed, used for various purposes, e.g. as lubricants for internal combustion engines of either spark-ignition or compression-ignition type, (as, for example, engines equipping cars or trucks, two-stroke engines, aircraft piston engines, marine engines or railway Diesel engines). Moreover, the fluids for automatic transmission, for gears, for metal working, for hydrauic applications and the greases may also take advantage of the incorporation of the additives of the invention.

Normally, the compositions of the invention are used in admixture with other conventional additives. The latter include phosphorus or sulfur containing extreme-pressure agents, organo-metallic detergents such as sulfide phenates, sulfonates and salicylates of alkaline-earth metals, ashless dispersants, thickening polymers as well as antifreeze agents, oxidation inhibitors, anti-corrosive, anti-rust, anti-foam agents and various other agents.

The following examples illustrate the invention without limiting the scope thereof.

EXAMPLE 1

20 g of polyisobutenyl succinic anhydride containing 0.0715 anhydride group per 100 g (i.e. the equivalent of 0.0143 anhydride group), and then 3.14 g of p.nonylphenol (0.0143 mole) and 0.67 g (0.0048 mole) of hexamethylenetetramine are introduced into a reaction vessel provided with a stirrer, a thermometer and a return condenser. The mixture is heated to 190° C., under stirring, for 1 h 30 minutes. The reaction product is a limpid dark-yellow viscous liquid, called additive I.

This additive is dissolved in a proportion of 5% by weight into 200 Neutral Solvent mineral oil, and its dispersing efficiency is estimated by the test of the spot on filter paper, in the presence of carbonaceous material recovered from Diesel engine used oil. The ratio of the diameter of the black spot to the oil aureole is 0.67.

The so-called "spot test" whose results are given in this example and in the following examples 2–4 consists in depositing a drop of oil containing the additive and carbon black on a sheet of filter paper, and calculating after 24 hours the ratio of the diameter of the carbon black spot on the diameter of the oil spot. The method is described with full detail by V. A. Gates et al V. A. et al. in SAE Preprint 572 (1955) or by A. SCHILLING in "Les huiles pour moteurs et le graissage des moteurs" Eds Technip, Tome 1, P. 89 (1962).

EXAMPLE 2

20 g of polyisobutenylsuccinic anhydride as used in example 1 (i.e. 0.0143 gram equivalent of anhydride) are condensed in the same operating conditions as in example 1, with 3.74 g (0.0143 mole) of p.dodecylphenol and 0.67 g (0.0048 mole) of hexamethylenetetramine. Additive II is thus obtained; the ratio of the diameters in a spot test similar to that of example 1 is 0.65.

EXAMPLE 3

Example 1 is repeated except that p.nonylphenol is replaced with 2.95 g (0.0143 mole) of 2,6-di-tert-butylphenol, thus giving additive III. After dilution at a 5% by weight concentration in a 100 Neutral mineral oil, the resultant solution is filtered. The spot test gives a ratio of 0.60.

EXAMPLE 4

A mixture comprising 40 g of polyisobutylsuccinic anhydride as in example 1 (equivalent to 0.0286 anhydride group), 3.14 g of p.nonylphenol (0.0143 mole), 1.4 g (0.01 mole) of hexamethylenetetramine and 45 g of 100 Neutral solvent mineral oil, is heated for 1 h 30 at 190° C. After filtration under pressure, a limpid and light brown coloured solution of additive IV is obtained. The dispersivity value as determined by the spot test is 0.67.

EXAMPLE 5

The products prepared in examples 1 to 4 are subjected to a coking test in order to determine the thermal stability of the additive and its dispersing efficiency. This test consists of projecting the additive-containing oil for 20 hours on the external wall of a metal beaker heated to 310° C., according to an ANTAR method. At the end of this test, the weight of deposit sticked on the metal surface is determined and the aspect of this deposit on the bottom and on the skirt of the beaker is observed.

The results, compared with those obtained with an industrial additive of bis(alkenylsuccinimide) type, are given in Table A below. The oil consists of a mixture of 350 Neutral and Bright Stock in a ratio by weight of 92/8 and has in each test a 5% by weight content of the additive to be tested and 1% by weight of oxidation inhibitor of the zinc dialkyldithiophosphate type.

TABLE A

| | Coking test | | | | |
|---|---|---|---|---|---|
| Dispersant additive | Ref. | Additive I | Additive II | Additive III | Additive IV |
| Weight of the deposit in mg | 660 | 630 | 600 | 560 | 580 |
| Bottom aspect/10 | 4.5 | 4.5 | 5 | 5 | 5 |
| Skirt aspect/10 | 6.5 | 8 | 8 | 7.5 | 7.5 |
| Oil consumption in g | 70 | 75 | 72 | 80 | 76 |

EXAMPLE 6

The dispersant additives I and IV according to the invention are tested on a Petter $AV_1$ Diesel engine, so as to determine both their dispersion efficiency and their thermal stability and to compare them with those obtained with the additive of reference described in example 5.

The method used with Petter $AV_1$ engine is standardized under reference No IP 175/69 and lasts 120 hours.

The test results are given in Table B below:

TABLE B

| | Tests on Petter $AV_1$ engine | | |
|---|---|---|---|
| Dispersant additive | Reference | Additive I | Additive IV |
| Mark of the deposit on the piston | | | |
| Average piston land/grooves/10 | 8.85 | 9.2 | 9.0 |
| Bottom | 6.5 | 7.5 | 7.2 |
| Mark of sludge on the cold parts of the engine | | | |
| Pushrods cover plate | 6.4 | 8.5 | 8.1 |
| Rocker-arms cover plate | 8.2 | 9.0 | 9.6 |

These results show improved dispersion effect and thermal stability for the additive compositions of the invention.

What is claimed as the invention is:

1. An additive composition having a dispersing effect in lubricating oils obtained by simultaneously reacting at least one alkenyl or polyalkenyl succinic anhydride containing 5 to 250 carbon atoms with at least one alkylphenol and with hexamethylenetetramine, wherein the molar ratio of said anhydride to alkylphenol is about 1:1 to 2:1, and the molar ratio of hexamethylenetetramine (expressed as amine groups) to anhydride is about 1.2:1 to 2:1.

2. An additive composition according to claim 1, characterized in that said substituted succinic anhydride is obtained by reacting a polymer of $C_2$–$C_5$ monoolefin with maleic anhydride, said polymer having a molecular weight from 500 to 1600.

3. An additive composition according to claim 2, characterized in that said polymer is polyisobutene.

4. An additive composition according to claim 1, characterized in that said alkylphenol is a phenol substituted with at least one linear or branched alkyl group, having from 4 to 12 carbon atoms, in ortho and/or in para position with respect to the hydroxyl group.

5. An additive composition according to claim 4, characterized in that said alkylphenol is selected from o.- and p.-nonylphenols, o.- and p.-dodecylphenols, 2,4- and 2,6-ditert-butyl phenols, p-hexylphenol, p-heptylphenol and p-octylphenol.

6. An additive composition according to claim 1, characterized in that said reaction is performed at a temperature from 120° to 250° C. for 1 to 3 hours.

7. An additive composition according to claim 1, characterized in that said reaction takes place in oil.

8. A lubricant composition characterized in that it contains a major proportion of a lubricant base and, as additive, at least one composition according to claim 1, in a proportion from 0.1 to 20% by weight with respect to said lubricant base.

9. An additive composition according to claim 1, wherein the succinic anhydride is the product obtained by condensing a maleic anhydride with an unsaturated, linear or branched, olefinic or polyolefinic unsaturated hydrocarbon having at least one unsaturation per molecule and comprising from 5 to 250 carbon atoms.

10. An additive composition according to claim 1, wherein the succinic anhydride is the product obtained by condensing a maleic anhydride with an unsaturated, linear or branched, halogenated olefinic or polyolefinic unsaturated hydrocarbon having at least one unsaturation per molecule and comprising from 5 to 250 carbon atoms.

11. An additive composition having a dispersing effect in lubricating oils, obtained by simultaneously reacting at least one alkenyl or polyalkenyl succinic anhydride containing 5 to 250 carbon atoms with at least one alkylphenol and with hexamethylenetetramine, with a molar proportion of the succinic anhydride of 1/1 to 2/1 with respect to the molar proportion of the alkylphenol, and with a molar proportion of hexamethylenetetramine, expressed as amine groups, of 1.2 to 2 with respect to the molar proportion of the succinic anhydride, and said reaction having been performed at a temperature of 120° to 250° C. for 1 to 3 hours.

12. An additive composition according to claim 11, wherein said reaction was conducted in oil.

13. An additive composition according to claim 11, wherein the succinic anhydride is the product obtained by condensing a maleic anhydride with an unsaturated, linear or branched, olefinic or polyolefinic unsaturated hydrocarbon having at least one unsaturation per molecule and comprising from 5 to 250 carbon atoms.

14. An additive composition according to claim 13, characterized in that said succinic anhydride is obtained by reacting a polymer of $C_2$–$C_5$ monoolefin with maleic anhydride, said polymer having a molecular weight from 500 to 1600.

15. An additive composition according to claim 14, characterized in that said polymer is polyisobutene.

16. An additive composition according to claim 11, characterized in that said alkylphenol is a phenol substituted with at least one linear or branched alkyl group, having from 4 to 12 carbon atoms, in ortho and/or in para position with respect to the hydroxyl group.

17. An additive composition according to claim 16, characterized in that said alkylphenol is selected from o.- and p.-nonylphenols, o.- and p.-dodecylphenols, 2,4- and 2,6-ditert-butyl phenols, p-hexylphenol, p-heptylphenol and p-octylphenol.

18. A lubricant composition characterized in that it contains a major proportion of a lubricant base and, as additive, at least one composition according to claim 11, in a proportion from 0.1 to 20% by weight with respect to said lubricant base.

* * * * *